(12) United States Patent
Sickenberger et al.

(10) Patent No.: US 9,689,792 B1
(45) Date of Patent: Jun. 27, 2017

(54) BIOLOGICAL MATERIAL DETECTION APPARATUS

(75) Inventors: David W. Sickenberger, Bel Air, MD (US); Christopher J. Karwacki, Churchville, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 650 days.

(21) Appl. No.: 13/010,190

(22) Filed: Jan. 20, 2011

Related U.S. Application Data

(60) Provisional application No. 61/297,059, filed on Jan. 21, 2010.

(51) Int. Cl.
| | |
|---|---|
| *G01N 21/00* | (2006.01) |
| *G05B 1/00* | (2006.01) |
| *F01N 3/28* | (2006.01) |
| *C12Q 1/00* | (2006.01) |
| *G01N 33/00* | (2006.01) |
| *G01N 7/00* | (2006.01) |

(52) U.S. Cl.
CPC .................................. *G01N 21/00* (2013.01)

(58) Field of Classification Search
CPC ............... G01N 15/06; G01N 15/0656; G01N 15/1434; G01N 15/1459; G01N 2015/0088; G01N 2015/0693; G01N 21/0303; G01N 21/05; G01N 21/53; G01N 21/64; G01N 21/6486; G01N 2201/065
USPC ........ 422/82.05, 105, 107, 68.1; 435/4, 808; 356/337; 73/29.01
See application file for complete search history.

(56) References Cited

U.S. PATENT DOCUMENTS

2010/0267049 A1* 10/2010 Rutter et al. ................... 435/7.1
2011/0076735 A1*  3/2011 Jovanovich et al. ...... 435/173.3

* cited by examiner

*Primary Examiner* — Dean Kwak
(74) *Attorney, Agent, or Firm* — Ulysses John Biffoni

(57) ABSTRACT

A particle detection apparatus and method includes an excitation source having a first emission band that excites a sample and a second emission band; a first optical device connected to the excitation source and attenuates radiation emitted in the second emission band; an optical cavity adjacent to the first optical device, which includes a sample excited by radiation from the excitation source; a substrate coupled to the optical cavity and exposed to the radiation from the excitation source; a binding compound coupled to the substrate, which includes a ligand coupled to the substrate; and a capture material coupled to the ligand and capturing the sample; a second optical device connected to the substrate and attenuates radiation emitted in the first emission band; and an optical detector connected to the second optical device and detects radiation emitted in the second emission band.

14 Claims, 7 Drawing Sheets

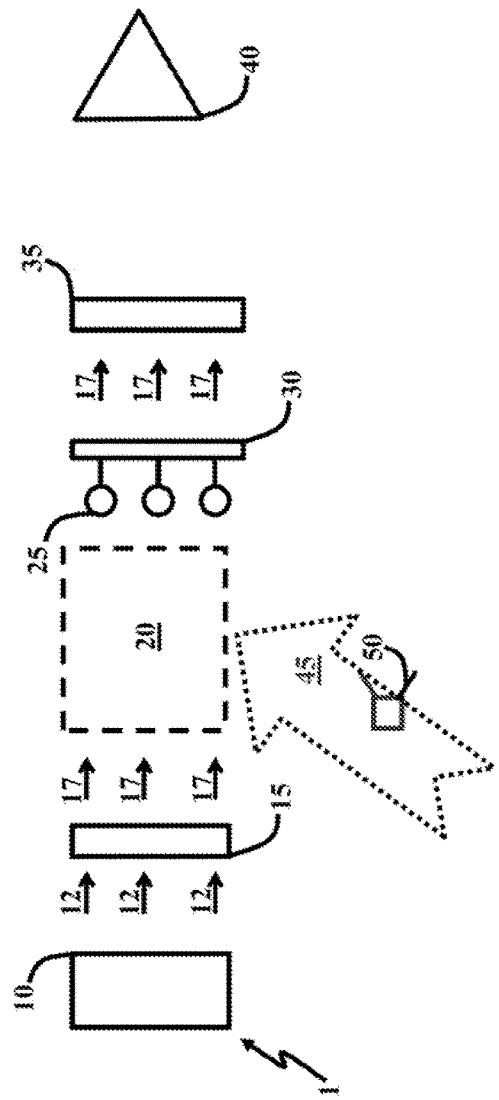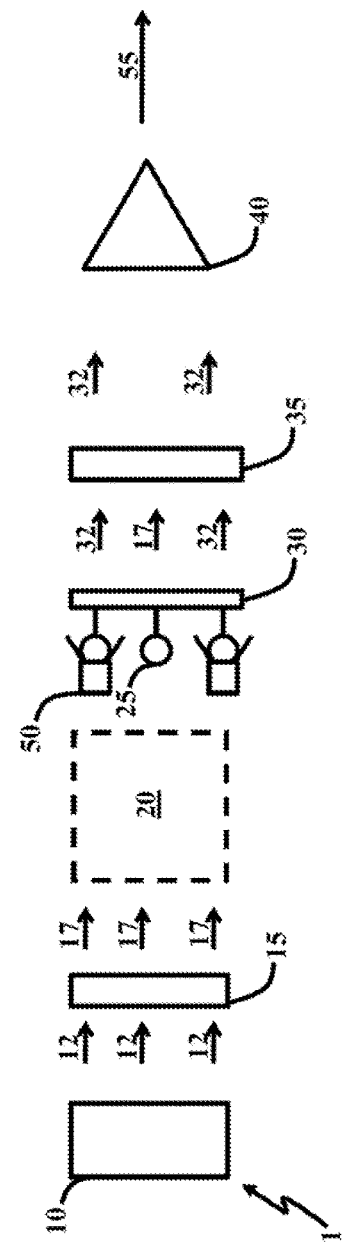

Figure 1:
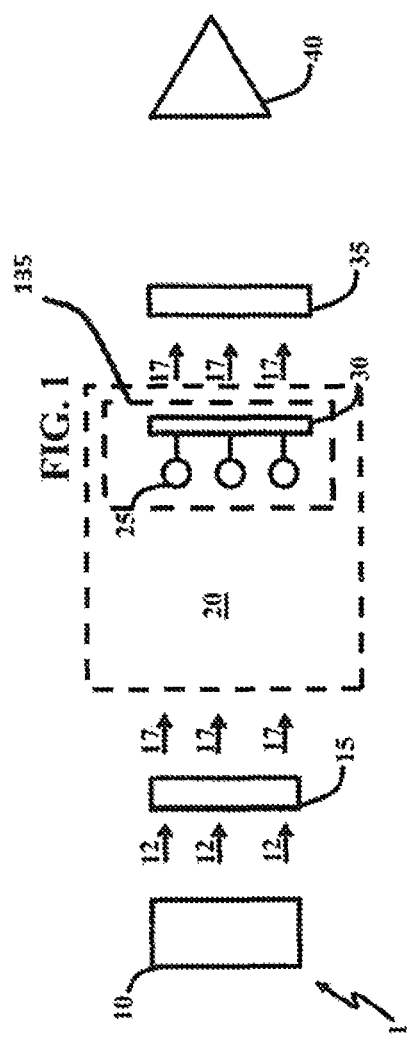

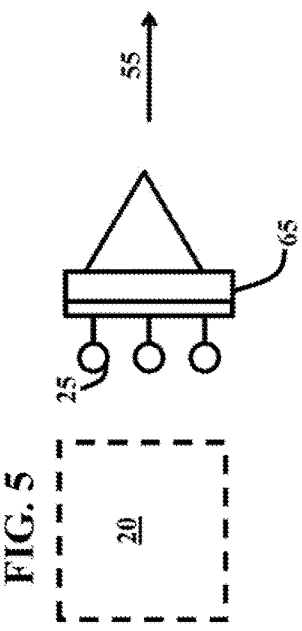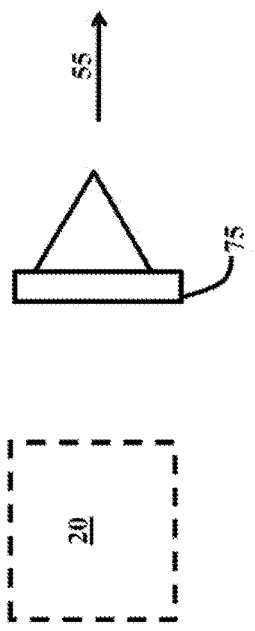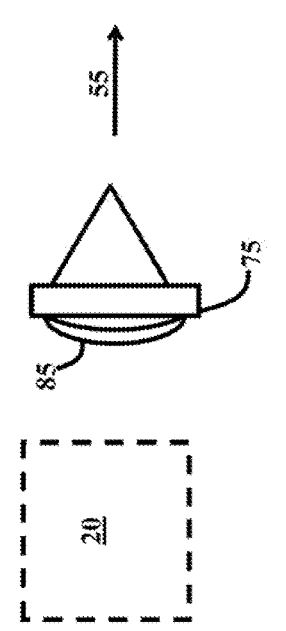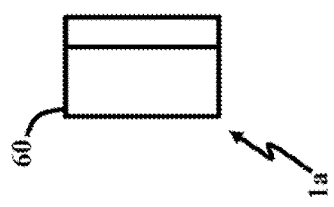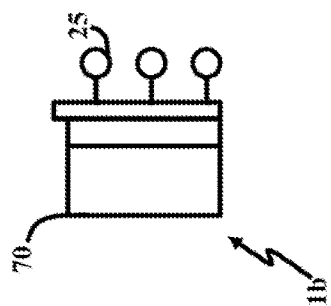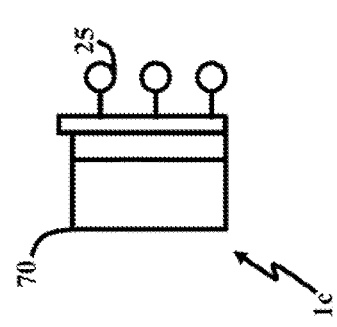
FIG. 5  FIG. 6  FIG. 7

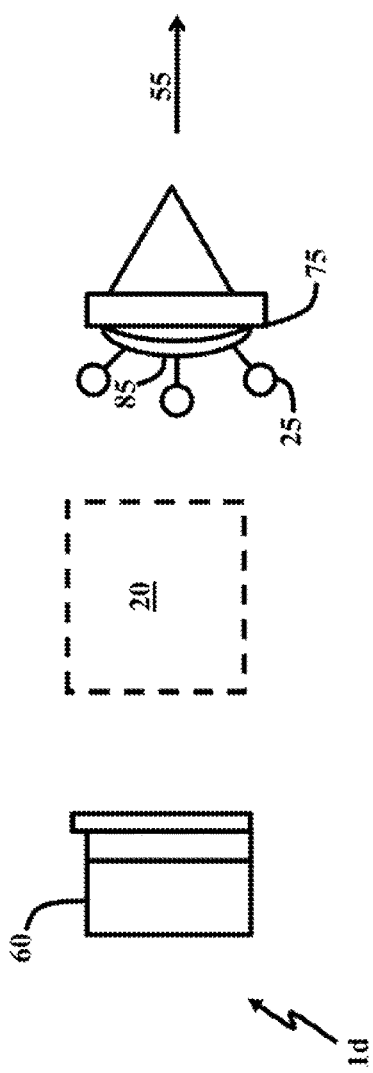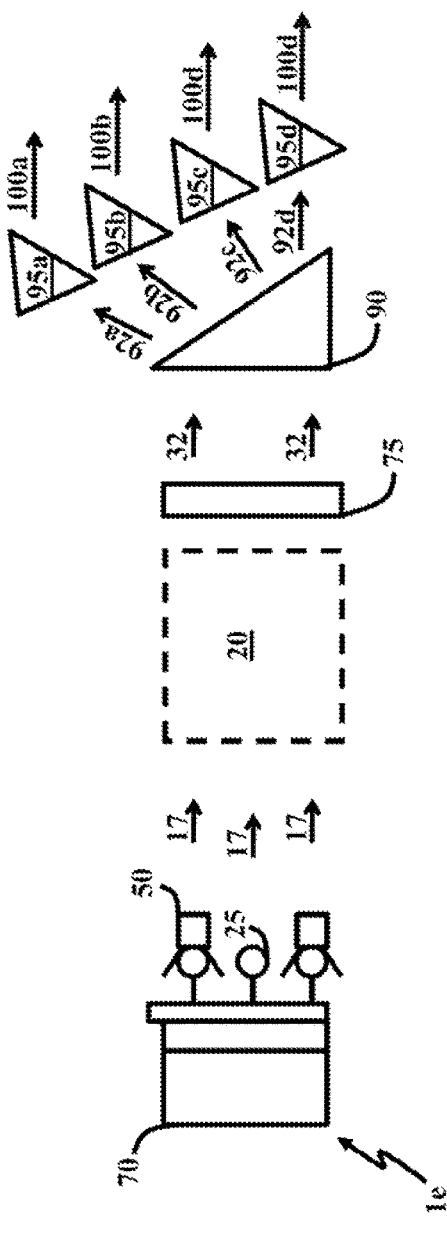

BIOLOGICAL MATERIAL DETECTION APPARATUS

RELATED APPLICATIONS

The application claims the benefit of priority from U.S. provisional patent application Ser. No. 61/297,059 filed an Jan. 21, 2010.

GOVERNMENT INTEREST

The embodiments described herein may be manufactured, used, and/or licensed by or for the United States Government.

BACKGROUND

Technical Field

The embodiments herein generally relate to particle detectors and, in particular, to micro ultraviolet (UV) particle detectors.

Description of the Related Art

It is well known that biological materials and organisms fluoresce under UV irradiation. UV light in the 380 nm wavelength range, for example, excites biological metabolic products such as nicotinamide adenine dinucleotide (NADH) and flavins to fluoresce in the visible range. In addition, higher energy UV light; e.g. 260 nm, excites proteins. Since vegetative and spore forms of bacteria contain these biochemicals, the bacteria will also fluoresce when irradiated with UV light. The fluorescent light can be detected using existing light detectors such as a photomultiplier tube (PMT).

Historically, biological aerosol detectors have been based on the exploitation of this phenomenon. These detectors typically use a pump to pull in ambient air containing the biological aerosols into some optical interrogation volume. An irradiative UV light, typically from a laser, light-emitting diode or xenon lamp, is directed to the particles. The bacterial particles thus excited will produce fluorescence light or photons. This light, in turn, travels outwards and hits a PMT or equivalent optical detector and produces an electrical, typically current or voltage, signal. The relevant and absolute magnitude of this detected signal can be used to determine the presence of a bacterial particle.

Consequently, conventional systems detect a fluorescent signal from aerosol in flow-through based designs. In such conventional systems, the aerosol particles are irradiated with UV light and the resultant signal collected and analyzed. This could be accomplished by interrogating the fluorescent signal observed from individual or multiple particles. Conventional systems may also include aerosols that have been impacted onto surfaces and then analyzed as a bulk sample. In such conventional systems, non-specific physical methods such as virtual impaction may be employed based on physical characteristics of the aerosols.

As a result, the interrogated sample would contain contributions from all material having similar physical properties. For example, a 3 μm anthrax aerosol would be collected at the same rate as a 3 μm dirt particle. The contribution of these potential non-threat materials to the observed fluorescent signal limits the application of this approach.

Alternatively, conventional systems can be aqueous-based devices that capture specific biological agent and materials on surfaces for interrogation. Aqueous-based devices are classically executed using an antigen-antibody approach. In such conventional systems, the antibody or similar capture material is placed on a substrate. A solution containing the suspected biological agent or threat material is then placed in contact with the coated substrate. The agent or threat material then attaches to the substrate via the antibody bridge. To detect the suspected biological agent, an additional dye is added to the solution, and the result dye is washed. The resultant dyed material, when excited with a wavelength corresponding to the optical properties of the dye, produces a detectable signal.

For the reasons stated above, and for other reasons stated below which will become apparent to those skilled in the art upon reading and understanding the present specification, there is a need in the art for alternative particle detectors for detecting biological agent aerosols.

SUMMARY

In view of the foregoing, an embodiment herein provides a particle detector comprising an excitation source having a first emission band and a second emission band, wherein the first emission band excites a sample, wherein the sample comprises any of a biological and chemical sample; a first optical device operatively connected to the excitation source, wherein the first optical device attenuates radiation emitted in the second emission band; an optical cavity adjacent to the first optical device, wherein the optical cavity comprises the sample excited by radiation from the excitation source; a substrate coupled to the optical cavity, wherein the substrate is exposed to the radiation from the excitation source; a binding compound coupled to the substrate, wherein the binding compound comprises a ligand coupled to the substrate; and a capture material coupled to the ligand, wherein the capture material captures the sample; a second optical device operatively connected to the substrate, wherein the second optical device attenuates radiation emitted in the first emission band; and an optical detector operatively connected to the second optical device, wherein the optical detector detects radiation emitted in the second emission band.

In such an apparatus, the excitation source may comprise a semiconductor ultraviolet optical source and, wherein the first emission band is within the ultra-violet spectrum. Moreover, the ligand may comprise any of an amino, carboxyl, and thiol group. Furthermore, the capture material may comprise a metal nano-particle. In addition, the capture material may comprise at least one of aliphatic-based polymers and aerosolized therapeutic proteins. Additionally, the capture material may comprise hydroxyl apatite.

Additionally, in such an apparatus, the excitation source, the first optical device, the substrate, and the binding compound may be arranged to form an emitter assembly. Furthermore, the optical detector may comprise an avalanche photodiode. Moreover, the optical detector comprises a lens.

Another embodiment herein provides a bio-dosimeter comprising an air chamber; an emitter assembly coupled to the air chamber, wherein the emitter assembly comprises an emission source having a first emission band exciting a threat material; a detector assembly coupled to the air chamber, wherein the detector assembly comprises a first optical device operatively connected to the air chamber, wherein the first optical device attenuates radiation emitted in the first emission band; and an optical detector operatively connected to the first optical device; and a capture assembly positioned between the emitter assembly and the detector assembly, wherein the capture assembly captures a sample of material, and wherein the capture assembly comprises a substrate operatively connected to the air chamber, a ligand operatively connected to the substrate; and a capture material operatively connected to the ligand.

In such a system, the emitter assembly may be combined with the capture assembly to form an emitter-capture assembly. Furthermore, the emission source may comprise a laser. In addition, the excitation source may comprise a second emission band, the first emission band may excite the sample of material, the sample of material may comprise any of a biological and chemical sample, and the emitter assembly may comprise a second optical device that attenuates radiation emitted in the second emission band.

Additionally, in such a system, the capture material may comprise at least one of aliphatic-based polymers and aerosolized therapeutic proteins. Moreover, the capture material may capture the sample utilizing at least one of a van der Waals force and a capillary force. Furthermore, the capture material may comprise a non-fluorescent material that selectively binds to aerosol particles entering the air chamber. In addition, the detector assembly may comprise a prism operatively connected to the detector assembly, and a plurality of optical detectors operatively connected to the prism, and where the plurality of optical detectors detect wavelengths of light corresponding to an optical output of the prism. In addition, such a system may further comprise an attachment mechanism. Moreover, at least one of the emitter assembly and the detector assembly may comprise solid-state components.

An embodiment herein also provides a bio-dosimeter comprising a protective housing, wherein the protective housing comprises and encloses an air chamber; an emitter assembly coupled to the air chamber, wherein the emitter assembly comprises an emission source having a first emission band exciting a material; a detector assembly coupled to the air chamber, wherein the detector assembly comprises a first optical device operatively connected to the air chamber, wherein the first optical device attenuates radiation emitted in the first emission band; an optical detector operatively connected to the first optical device; and a capture assembly positioned between the emitter assembly and the detector assembly, wherein the capture assembly captures a sample, and wherein the capture assembly comprises a substrate operatively connected to the air chamber, a ligand operatively connected to the substrate; and a capture material operatively connected to the ligand; an air passage bored through the protective housing; a fan within the air passage; and an attachment device operatively connected to the protective housing.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 1 illustrates a schematic diagram of a particle detector according to an embodiment herein;

FIG. 2 illustrates a schematic diagram of a binding compound and substrate according to an embodiment herein;

FIG. 3 illustrates a schematic diagram of a particle detector in ambient air according to an embodiment herein;

FIG. 4 illustrates a schematic diagram of a particle detector encountering aerosol particles according to an embodiment herein;

FIG. 5 illustrates a schematic diagram of an alternative particle detector according to an embodiment herein;

FIG. 6 illustrates a schematic diagram of an alternative particle detector, where a substrate and binding compound are applied to an emission device, according to an embodiment herein;

FIG. 7 illustrates a schematic diagram of an alternative particle detector with a lens according to an embodiment herein;

FIG. 8 illustrates a schematic diagram of an alternative particle detector, where a substrate and binding compound are applied to an emission device and lens combination, according to an embodiment herein;

FIG. 9 illustrates a schematic diagram of an alternative particle detector with a prism according to an embodiment herein;

FIG. 10 illustrates a schematic diagram of an alternative substrate according to an embodiment herein;

FIG. 11 illustrates a perspective schematic diagram of an alternative bio-dosimeter according to an embodiment herein; and FIG. 12 illustrates a diagram of the bio-dosimeter shown in FIG. 11 with the protective housing removed according to an embodiment herein.

DETAILED DESCRIPTION OF PREFERRED EMBODIMENTS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide a low-cost particle detector, which is portable and lightweight. For example, particle detectors according to the embodiments described below are capable of being attached to clothing. Referring now to the drawings, and more particularly to FIGS. 1 through 12, where similar reference characters denote corresponding features consistently throughout the figures, there are shown preferred embodiments.

FIG. 1 illustrates a schematic diagram of a particle detector 1 according to an embodiment herein. As shown, particle detector 1 includes an emitter 10, a short-pass filter 15, an optical cavity 20, a binding compound 25, a substrate 30, a long-pass filter 35, and an optical detector 40. In the embodiment shown in FIG. 1, emitter 10 includes a UV optical light source that produces a wavelength necessary to excite fluorescence in a sample (not shown) (e.g., a threat material or biological agent). For example, the wavelengths necessary to excite fluorescence in a sample may be in the 260 nm to 380 nm range. Such a device may be commercially available, (e.g., a 365 nm Light Emitting Diode available from Nichia Corporation, Tokushima, Japan), which reduces the overall cost of particle detector 1 by avoiding additional manufacturing costs. In the embodiment shown in FIG. 1, emitter 10 emits radiation (e.g., light 12) that contains wavelengths longer that UV light. Therefore, in FIG. 1, emitter 10 emits radiation towards short-pass filter 15, which is configured to attenuate (or otherwise remove) these longer wavelengths. Those skilled in the art, however, would recognize that the combination of emitter 10 and short-pass filter 15 may be substituted for a narrow-band light source—such as a laser emitting radiation within the desired wavelength. Therefore, the embodiment shown in FIG. 1 is not limited to the configuration of emitter 10 and short-pass filter 15 shown.

After passing through short-pass filter 15, the filtered radiation (e.g., filtered light 17) is directed towards optical cavity 20 (e.g., an air chamber) housed within particle detector 1. In the embodiment shown in FIG. 1, the filtered radiation (e.g., filtered light 17) directly strikes binding component 25 first and then substrate 30, to which binding component 25 is attached. While not shown in FIG. 1, substrate 30 in the embodiment of FIG. 1 is constructed of a material that will allow fluorescence light to pass through it but will not, in itself fluoresce. Quartz is an example of such a material. Binding component 25, as described in further detail below, modifies the surface of substrate 30 that points towards optical cavity 20. The binding component 25 and the substrate 30 together comprise the capture assembly 135 as depicted in FIG. 1.

Since substrate 30 is preferably transparent, UV light 17 passes therethrough and is directed to long-pass filter 35. In the embodiment shown in FIG. 1, long-pass filter 35 attenuates (or otherwise removes) UV light 17. Thereafter, any unfiltered radiation (not shown) is directed towards optical detector 40.

In the case where no biological agent or threat materials are present in optical cavity 20 (and thereby not captured by binding compound 25, as described below), the light impacting binding component 25 and substrate 30 will pass through and exit as non-fluorescence inducing light (e.g., UV light 17). This light will travel to long pass filter 35 and will be removed. Consequently, no light will pass to the optical detector 40 and no fluorescence signal output will be produced.

Figure 2:
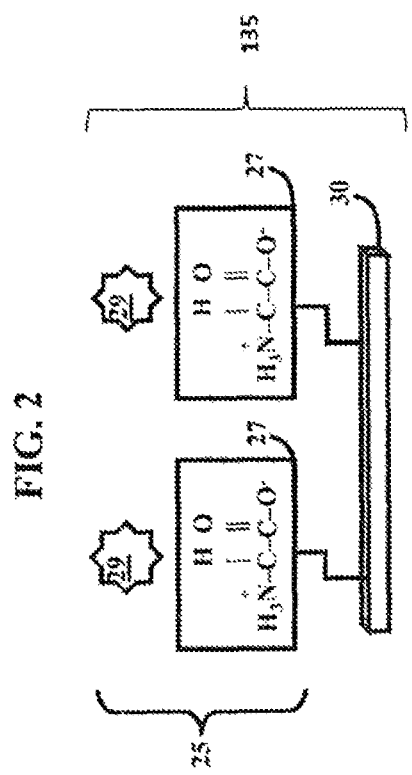
Figure 10:
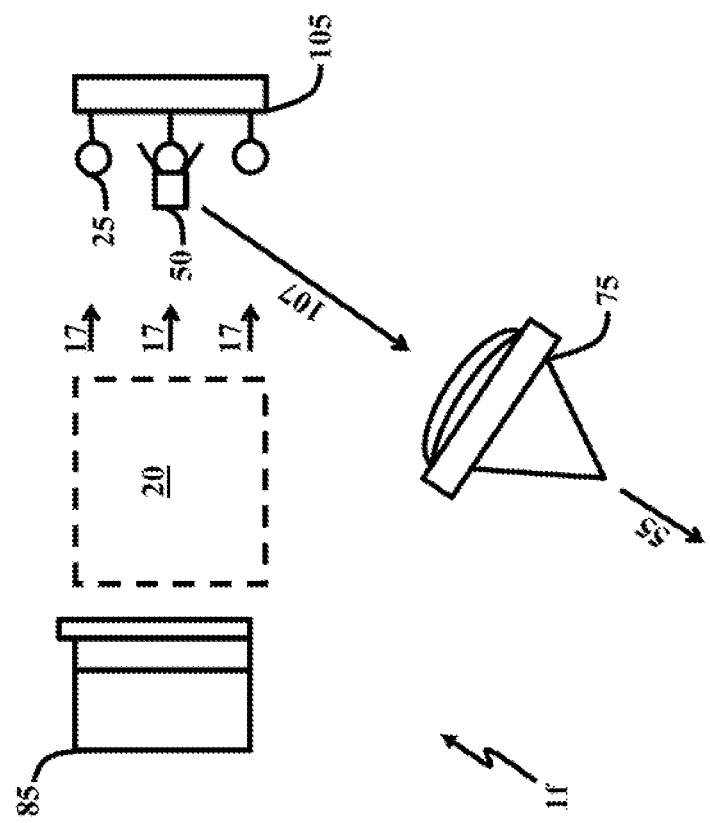

As described above, binding component 25 has several qualities. FIG. 2, with reference to FIG. 1, illustrates a schematic diagram of a binding compound 25 and a substrate 30 according to an embodiment herein. As shown in FIG. 2, binding compound 25 includes a ligand 27 that attaches itself to substrate 30. In addition, a capture material 29 attaches itself to ligand 27. In the embodiment shown in FIG. 2, capture material 29 includes metal (e.g., gold) nano-particles.

As shown in FIG. 2, binding compound 25 attaches to substrate 30 and adheres to substrate 30 when exposed to open-air environmental factors; such environmental factors include, but are not limited to high humidity, temperature extremes, and changes thereof. In addition, binding compound 25 does not produce a fluorescent signal that might mask the fluorescent signal produced from a target material (e.g., a biological agent or other threat material, as discussed below). Consequently, the fluorescence profile of binding compound 25 maps away from the target material. In addition, as described in further detail below, binding compound 25 includes some binding properties (e.g., through capture material 29) to the target material.

In FIG. 2, capture material 29 (e.g., metal nano-particles) is coupled with ligand 27 groups dispersed on substrate 30, which provides a tunable capture and sense platform for various target materials (e.g., biological agents). For example, metal nano-particles (e.g., gold nano-particles), in the range of 1 nm to 50 nm, can be used as capture material 29 and provide properties that can enhance plasmonic activity (optical absorbance), van der Waals binding (non-reactive) and electrostatic/covalent bonding to promote a reaction based on the metal type, particle size and shape. In addition, while not shown in FIG. 2, substrate 30 is porous in an alternative embodiment.

As discussed below, the growth, dispersion and activity of capture material 29 (e.g., metal nano-particles) is manifested by providing an optimal chemical environment for capture material 29 through use of chemical ligands (e.g., ligand 27). For example, ligand 27 includes, but is not limited to amino, carboxyl and thiol groups grafted to substrate 30. In the embodiment shown in FIG. 2, ligand 27 is dispersed onto substrate 30 and enables capture material 29 (e.g., metal nano-particles) to bind preferentially thereto. In addition, ligand 27 can be stabilized to minimize migration and annealing of capture material 29 (e.g., metal nano-particles). In particular, ligand-bound metal nano-particles (i.e., capture material 29) are known to provide enhanced activity due to charge transfer between the substrate (i.e., substrate 30), ligand (i.e., ligand 27), and metal particle (i.e., capture material 29). Moreover, porosity of substrate 30 (as described above) can be controlled to facilitate dispersion of chemical surface groups and is an important variable in controlling the concentration of active metal sites and binding with the target material (e.g., biological materials).

In addition to metal nano-particles shown in FIG. 2, alternatives to capture material 29 exist. The alternative embodiments of capture material 29 described below are intended to be non-limiting examples and further alternatives exist, but are not described below yet are nevertheless readily apparent to those skilled in the art.

Hydroxyl apatite, a non-fluorescent inorganic, can capture aerosolized biological materials—including bacteria and viruses. Chemicals added to the external surface of the hydroxyl apatite inherently bind through normal polar/non-polar interactions. Additionally, peptides could be introduced to hydroxyl apatite to exploit antibody-antigen based binding. For example, non-aromatic amino acids, such as glycine, could be used to produce a protein that would not inherently fluoresce but have some core antibody capture capability.

Additional embodiments of capture material 29 use the adhesive properties of aerosolize particles to surfaces. Aliphatic-based polymers are an example of capture material 29 that uses this principal and does not exhibit significant fluoresce. Moreover, aerosolized therapeutic proteins exhibit different adhesion strengths between the protein and the various surfaces. Therefore such proteins can be bound onto polymeric and metallic surfaces to operate as another embodiment of capture material 29.

Furthermore, as discussed above, additional embodiments of capture material 29 utilize van der Waals and capillary forces to capture the intended target material. For example, hydrophilic-based capillary capture exhibit suitable adhesive forces. In addition, the non-metallic surfaces used according to this embodiment would not, by itself, fluoresce.

FIG. 3, with reference to FIGS. 1 and 2, illustrates a schematic diagram of particle detector 1 in ambient air, according to an embodiment herein. In normal operation, ambient airflow 45 will pass into and over binding component 25 and substrate 30 via the optical cavity 20. In an alternative embodiment not shown in FIG. 3, airflow 45 is artificially enhanced (e.g., via a pump, fan, or other mechanism/process). In addition, it is equally possible for particle detector 1 to allow natural convection to occur and thereby reducing the need for a pump to enhance airflow 45. As a result of airflow 45, threat material 50 (e.g., an aerosolized biological agent) will enter optical cavity 20.

FIG. 4, with reference to FIGS. 1 through 3, illustrates a schematic diagram of particle detector 1 in contact with threat material 50, according to an embodiment herein. As shown in FIG. 4, while in optical cavity 20, threat material 50 will encounter binding component 25 and attach to it via capture material 29 (as shown in FIG. 2). When this attachment occurs, filtered UV light 17 (e.g., as emitted from emitter 10 and filtered through short-pass filter 15) impacting the bounded threat material 50 (e.g., biological agent) will fluoresce. As a result of this fluorescence, long wavelength emissions (e.g., visible light 32) will be produced. Since bonding compound 25 is coupled to a transparent substrate 30 in the embodiment shown in FIG. 4, these longer wavelengths are directed and pass through long-pass filter 35 along with the filtered UV light 17. Long-pass filter 35 is configured to attenuate (or otherwise remove) long wavelengths (e.g., UV light 17) so that the result is predominately the fluorescent light produced by the fluorescing material (e.g., threat material 50). This light is directed to optical detector 40, resulting in fluorescent signal 55. In practice, the embodiment shown in FIG. 4 will be subjected to multiple attachments of threat material 50 to capture material 29 over long time periods; e.g., minutes or even hours. As a result, fluorescent signal 55 will result from a number of bindings. This will increase the total observed fluorescent signal 55.

Consequently, in one embodiment herein, optical detector 40 is a low cost optical detector (e.g., Avalanche Photodiodes or "APD"). Such an embodiment provides an opportunity to utilize low cost components in particle detector 1 and reduce the overall cost of particle detector 1. In addition, the ability to examine the fluorescence as measured over a long sampling time also provides the means of measuring the exposure or dose over that time.

In an alternative embodiment, the attachment of threat material 50 (e.g., a biological aerosol) to binding component 25 (e.g., via capture material 29) is enhanced by applying a voltage or electrostatic field on substrate 30. For example, some threat materials (e.g., man-made aerosols) have a net charge. An electrostatic field can, therefore, be used to move and capture such charges. In an additional embodiment, the same electrostatic field is also used to pump charged particles into the detector.

In yet another embodiment, the core components described can be distilled to some integrated, solid-state items, as illustrated in FIGS. 5 through 8, with reference to FIGS. 1 through 4. For example, illustrated in particle detector 1*a* shown in FIG. 5, light emitting diode (LED) UV emission source 60 is fabricated with an integrated short-pass filter (e.g., short-pass filter 15, shown in FIG. 1). Similarly, detector 65 is fabricated to incorporate a long-pass filter (e.g., long-pass filter 35, shown in FIG. 1) and a binding component (e.g., binding compound 25, shown in FIG. 2) applied to a substrate (e.g., substrate 30, shown in FIG. 2). The benefit offered by the embodiment shown in FIG. 5 is manufacturing simplicity, which translates to low cost. FIG. 6, with reference to FIGS. 1 through 5, illustrates an alternative embodiment which is a modification of the embodiment presented in FIG. 5, where a substrate (e.g., substrate 30, shown if FIG. 2) and binding component (e.g., binding compound 25, shown in FIG. 2) have been applied to emission source 70 of particle detector 1*b*. In addition, detector assembly 75 is fabricated to incorporate a long-pass filter (e.g., long-pass filter 35, shown in FIG. 1). FIG. 7, with reference to FIGS. 1 through 6, illustrates particle detector 1*c*, which provides a means of improving the optical collection efficiency of the detector 1*c* by incorporating a lens 85 with detector assembly 75 (shown in FIG. 6). FIG. 8, with reference to FIGS. 1 through 7, illustrates particle detector 1*d* and provides a further modification where a substrate (e.g., substrate 30, shown in FIG. 2) and binding component (e.g., binding compound 25, shown in FIG. 2) have been applied to lens 85, which is coupled to detector assembly 75. As an alternative embodiment to particle detector 1*d*, lens 85 also serves as a substrate (e.g., substrate 30, shown in FIG. 2) for the binding component (e.g., binding compound 25, shown in FIG. 2).

FIG. 9, with reference to FIGS. 1 through 8, illustrates particle detector 1*e*, which includes the addition of a prism 90 to disperse (e.g., dispersed light 92*a* through 92*d*) the fluorescent light (e.g., visible light 32) produced from the interaction threat material 50 and binding compound 25, as described above. In the embodiment shown in FIG. 9, after prism 90, dispersed light dispersed light 92*a* through 92*d* is directed to several independent optical detectors 95*a* through 95*d* and produces independent light wavelength signals (e.g., signals 100*a* through 100*d*). Consequently, when the fluorescent information provided by different threat materials 50 (e.g., biological agents) is different, the various signals (e.g., signals 100*a* through 100*d*) detected by optical detectors 95*a* through 95*d* provide an opportunity to improve discrimination and classification of threat material 50.

FIG. 10 illustrates a schematic diagram of alternative particle detector 1*f* that uses reflective substrate 105. In particle detector 1*f*, substrate 105 provides a binding surface for binding component 25. As described above, threat material 50 (e.g., an aerosolized biological agent or threat material) binds to the binding component 25 attached to the substrate 105. The bound threat material 50 fluoresces when excited with filtered UV light 17. This fluorescent light 107 then travels to the optical detector assembly 75. As described above, the optical detector 75 produces signal 55 in response to fluorescent light 105. Additional optical devices (not shown) can be used to improve the collection efficiency of the optical detector assembly 75 to collect the fluorescent light from the substrate 105. This includes modifying the surface of the substrate 105 to serve as a focusing surface or the addition of lenses.

The embodiments described herein present a unique utility in a number of different scenarios; a few non-limiting examples are described below.

Embodiments described herein with a non-specific capture capacity can be used in concert with other more specific bio-detectors. In such a scenario, the more specific detectors can identify that an event took place. The non-specific detector (e.g., particle detector 1) can be used to located and track the progress of the event. For example, a non-specific detector (e.g., particle detector 1) can be widely disseminated (e.g., coupled to clothing) to provide spatial information about the event. A particular, non-limiting example of such an application includes an air base with a very capable bio-detector being used to detect an attack. The cost, size, weight, and power limit the number of this grade of large-scale detectors that can be deployed on the base. The non-specific detectors described by the embodiment herein (e.g., particle detector 1) can supplement the large-scale detector installations and are widely disbursed on the base. The widely dispersed installation of the embodiments described herein is accomplished due the low cost, power, size, weight associated with these devices. In an example scenario, when an attack occurs, the large-scale bio detector is used to detect the attack. Subsequently, an operator then observes the rate of change in total bio mass on each of the widely disbursed, non-specific detectors according to the embodiments herein (e.g., particle detector 1). Consequently, the operator is able to ascertain which areas have become contaminated and those that are not. This information can, in turn, be used to reconfigure how the air base conducts a mission to minimize contact with contaminated areas.

An alternative application is in a hospital setting. For example, after the observation of a high concentration of a threat material in the waiting room, a hospital administrator improves the ventilation in those areas to reduce the concentration of the threat material. In general, a non-specific detector according to the embodiments herein (e.g., particle detector 1) could be used to trigger low impact, precautionary measures.

A third application of a non-specific detector according to the embodiments herein is where the air stream in a face (i.e. gas) mask first passes by or through the non-specific detector (e.g., particle detector 1). The normal air entering the mask should be clean of all aerosols, assuming the filters are functional. In the event the filters fails or are consumed, the number of particles passing to the wearer will increase. Consequently, a non-specific detector (e.g., particle detector 1) detects such a failure and alerts the user to the need to replace the filter or take other protective action.

In addition to the applications of the embodiments described herein discussed above, increasing the capture specific extends the capability and uses by increasing the confidence of the detection. For example, specificity allows the ability to isolate a reactionary measure; such as the choice of prophylaxis used to counter the threat. A few non-limiting applications of this utility are described below.

In one application, embodiments described herein are utilized as a bio-dosimeter. In this application, the bio-dosimeter is a small, wearable device (e.g., of a similar size to radiation dosimeters worn by personnel operating with radioactive sources or ionizing wavelengths, e.g. x-rays). For example, the bio-dosimeter alerts the individual and responsive medical personnel to the fact that an individual was exposed and the agent that was contacted.

Figure 11:
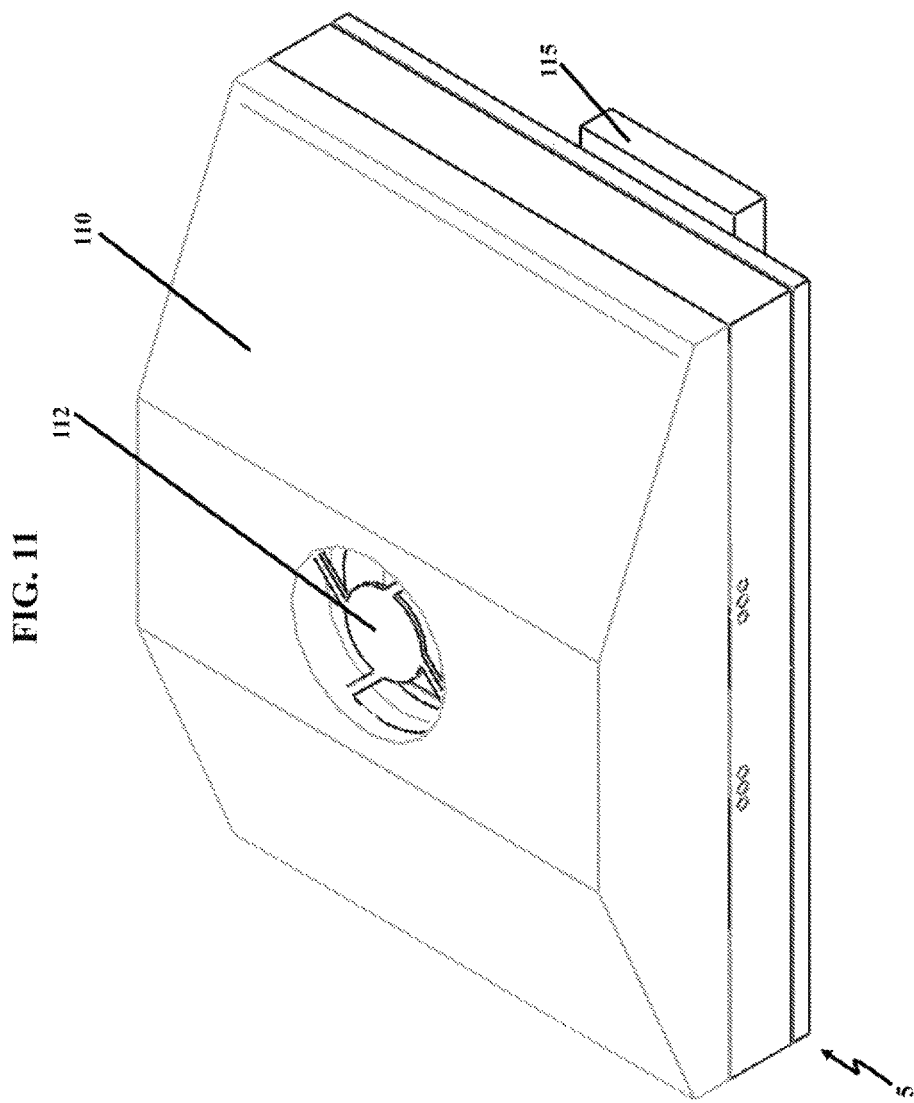
Figure 12:
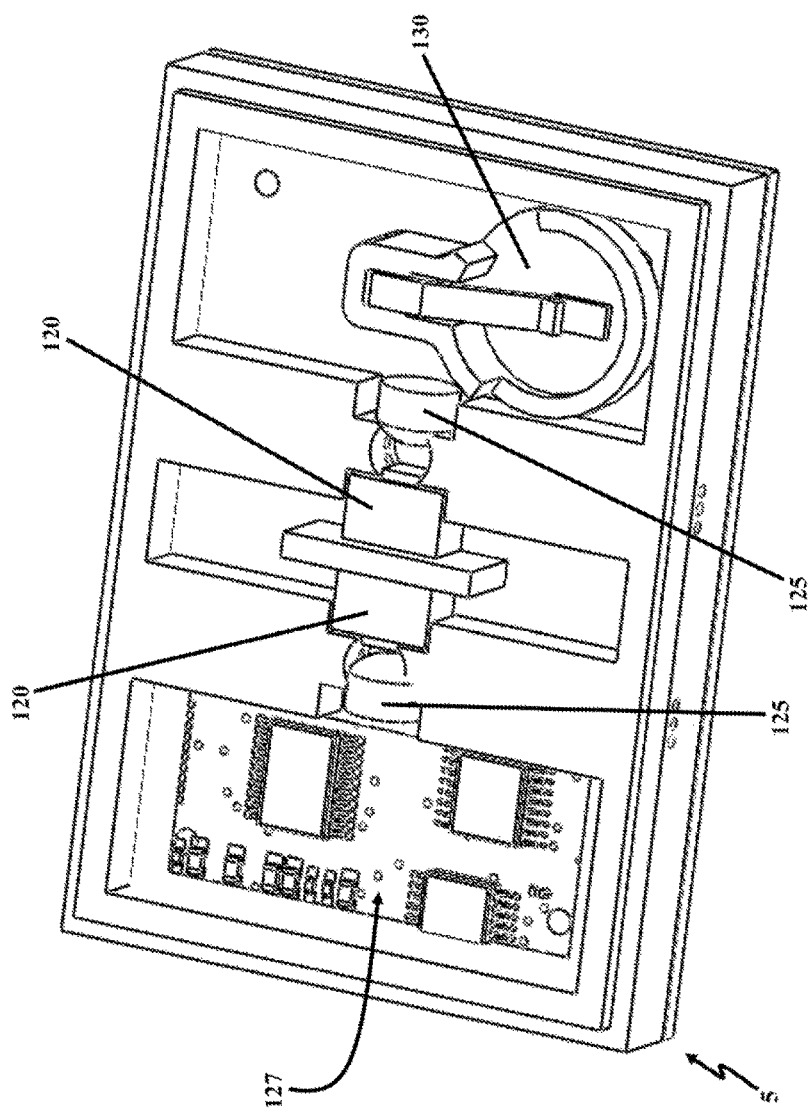

FIGS. 11 and 12, with reference to FIGS. 1 through 10, illustrate a schematic diagram of bio-dosimeter 5. As shown in FIG. 11, bio-dosimeter 5 includes a protective housing 110, a fan 112, and an attachment device (e.g., a clip, etc.) 115. In one embodiment, attachment device 115 attaches bio-dosimeter 5 to an article of clothing (not shown). FIG. 12 is a diagram of bio-dosimeter 5 with the protective housing 110 removed. As shown in FIG. 12, bio-dosimeter 5 includes a pair of LED emitters 120, a pair of APDs 125, APD possessing circuitry 127, and a battery 130 in operative connection with one another.

In an alternative application, a general dosimeter measures the transport and hazard within rooms and buildings. For example, these devices could be placed in every hospital room to measure the transport of an infectious disease within the hospital.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A biological material detector, comprising:
   an air chamber comprising a physical structure creating an enclosure;
   an emitter assembly operatively coupled to said air chamber, wherein said emitter assembly includes an emission source producing a wavelength of light to excite fluorescence in biological material;
   an optical detector, wherein said optical detector further comprises a prism operatively connected to said optical detector;
   means for capturing a sample of biological aerosol material from air in said air chamber, said means for capturing biological material positioned between said emitter assembly and said optical detector and contained within said air chamber, and wherein said means for capturing comprises a capture assembly which comprises: a substrate operatively connected to said air chamber; a ligand operatively connected to said substrate; and a capture material operatively connected to said ligand; and
   an optical filter positioned between said optical detector and said capture assembly, wherein said filter attenuates light wavelengths other than fluorescence light wavelengths produced by the fluorescing biological aerosol material; and
   wherein said optical detector is operatively connected to said capture assembly and said optical filter, and said detector is capable of detecting fluorescence generated directly by biological aerosol material captured on said capture assembly; and
   a protective housing enclosing said biological detector, an air passage bored through said protective housing.

2. The biological detector of claim 1, wherein said emission source comprises a laser producing ultraviolet light.

3. The biological detector of claim 1, wherein said emission assembly comprises a light source and an emission assembly optical filter adapted to attenuate light source wavelengths other than ultraviolet wavelengths.

4. The biological detector of claim 1, wherein said capture material comprises a non-fluorescent material that selectively binds to biological aerosol particles entering said air chamber.

5. The biological detector of claim 1, wherein said capture material captures said sample utilizing at least one of a van der Waals force and a capillary force.

6. The biological detector of claim 1, wherein said capture material comprises a metal nanoparticle.

7. The biological detector of claim 6, wherein said metal nanoparticle comprises a gold nanoparticle.

8. The biological detector of claim 1, wherein said capture material comprises aliphatic-based polymers and aerosolized therapeutic proteins.

9. The biological detector of claim 1, wherein said capture material comprises hydroxyl apatite.

10. The biological detector of claim 1, wherein said ligand comprises amino, carboxyl, or thiol groups grafted to said substrate.

11. The biological detector of claim 1, wherein said optical detector further comprises a plurality of additional optical detectors operatively connected to said prism, and wherein said plurality of optical detectors detect wavelengths of light corresponding to an optical output of said prism.

12. The biological detector of claim 1, wherein said biological detector includes an attachment mechanism.

13. The biological detector of claim 1, wherein at least one of said emitter assembly and said optical detector assembly comprise solid-state components.

14. The biological detector of claim 1, further comprising:
- a fan within said air passage for providing ambient air to said air chamber; and
- an attachment device operatively connected to said protective housing.

* * * * *